United States Patent
Sirimanne et al.

(12)

(10) Patent No.: US 6,356,782 B1
(45) Date of Patent: Mar. 12, 2002

(54) SUBCUTANEOUS CAVITY MARKING DEVICE AND METHOD

(75) Inventors: D. Laksen Sirimanne, Palo Alto; Douglas S. Sutton, Pacifica; Natalie V. Fawzi, Belmont; Gail Lebovic, Menlo Park, all of CA (US)

(73) Assignee: Vivant Medical, Inc., Mountain View, CA (US)

( * ) Notice: Subject to any disclaimer, the term of this patent is extended or adjusted under 35 U.S.C. 154(b) by 0 days.

(21) Appl. No.: 09/285,329

(22) Filed: Apr. 2, 1999

Related U.S. Application Data

(63) Continuation-in-part of application No. 09/220,618, filed on Dec. 24, 1998, now abandoned.

(51) Int. Cl.$^7$ .................................................. A61B 6/00
(52) U.S. Cl. ...................... 600/431; 600/432; 600/436; 128/899; 604/53; 604/265; 424/423; 424/426; 606/130; 606/194; 606/195
(58) Field of Search ................................ 600/407, 414, 600/420, 426, 431, 432, 436, 3, 4, 26.6, 36; 128/899; 623/1, 11, 12; 604/53, 265; 424/423, 426; 606/130, 194, 195

(56) References Cited

U.S. PATENT DOCUMENTS

| | | |
|---|---|---|
| 2,740,405 A | 4/1956 | Riordan |
| 2,972,350 A | 2/1961 | Deker |
| 4,114,601 A | 9/1978 | Abels |
| 4,202,349 A | 5/1980 | Jones |
| 4,230,123 A | 10/1980 | Hawkins, Jr. |
| 4,291,013 A | 9/1981 | Wahlig et al. |
| 4,347,234 A | 8/1982 | Wahlig et al. |
| 4,626,251 A | 12/1986 | Shen |
| 4,628,944 A | 12/1986 | MacGregor et al. |
| 4,636,208 A | 1/1987 | Rath |
| 4,639,253 A | 1/1987 | Dyer et al. |

(List continued on next page.)

FOREIGN PATENT DOCUMENTS

| | | |
|---|---|---|
| DE | 43 30 958 A1 | 3/1995 |
| DE | 44 03 789 A1 | 8/1995 |
| EP | 0 534 696 A1 | 3/1993 |

(List continued on next page.)

OTHER PUBLICATIONS

"The First FDA–approved Surgical Fibrin Sealant," *Tisseel VH Kit Firbirn Sealant,* Publication by Tisseel, 5 pages, date unknown.

Alesch et al., (1992) "Marking of the Stereotactic Target Point by a Radiopaque Silicone Sphere" *Acta Neurochirurgica* vol. 115, 149–151.

Brannon–Peppas, Lisa. (1997). "Polymers in Controlled Drug Delivery" *Medical Plastics and Biomaterials,* pp. 34–44.

(List continued on next page.)

*Primary Examiner*—Marvin M. Lateef
*Assistant Examiner*—Jeoyuh Lin
(74) *Attorney, Agent, or Firm*—Morrison & Foerster LLP

(57) ABSTRACT

These are subcutaneous cavity marking devices and methods. More particularly, upon insertion into a body, the cavity marking device and method enable one to determine the center, orientation, and periphery of the cavity by radiographic, mammographic, echogenic, or other non-invasive imaging techniques. Also, the device contains a bioabsorbable or non-bioabsorbable marker. The device may be combined with various substances enhancing the radiopaque, mammographic, or echogenic characteristics of the marker or the body allowing it to be observed by any non-invasive imaging techniques. This is further a method of marking a subcutaneous cavity using a bioabsorbable material and a bioabsorbable or non-bioabsorbable marker in conjunction with the material. The method also may combine any of the features as described with the device.

111 Claims, 10 Drawing Sheets

U.S. PATENT DOCUMENTS

| | | | |
|---|---|---|---|
| 4,645,499 A | | 2/1987 | Rupinskas |
| 4,704,109 A | | 11/1987 | Rupinskas |
| 4,718,897 A | | 1/1988 | Elves |
| 4,787,391 A | | 11/1988 | Elefteriades |
| 4,795,463 A | | 1/1989 | Gerow |
| 4,803,075 A | | 2/1989 | Wallace et al. |
| 4,812,120 A | | 3/1989 | Flanagan et al. |
| 4,852,568 A | | 8/1989 | Kensey et al. |
| 4,863,470 A | | 9/1989 | Carter |
| 4,917,694 A | | 4/1990 | Jessup |
| 4,944,308 A | | 7/1990 | Akerfeldt |
| 4,966,583 A | | 10/1990 | Debbas |
| 5,018,530 A | * | 5/1991 | Rank et al. ................. 600/435 |
| 5,041,103 A | | 8/1991 | Rupinskas |
| 5,045,080 A | | 9/1991 | Dyer et al. |
| 5,057,095 A | | 10/1991 | Fabian |
| 5,059,197 A | | 10/1991 | Urie et al. |
| 5,085,629 A | | 2/1992 | Goldberg et al. |
| 5,108,421 A | | 4/1992 | Fowler |
| 5,112,325 A | | 5/1992 | Zachry |
| 5,183,463 A | | 2/1993 | Debbas |
| 5,201,314 A | | 4/1993 | Bosley et al. |
| 5,207,705 A | | 5/1993 | Trudell et al. |
| 5,221,269 A | * | 6/1993 | Miller et al. ........... 604/170.03 |
| 5,275,616 A | | 1/1994 | Fowler |
| 5,301,682 A | | 4/1994 | Debbas |
| 5,326,350 A | | 7/1994 | Li |
| 5,329,944 A | | 7/1994 | Fabian et al. |
| 5,334,216 A | | 8/1994 | Vidal et al. |
| 5,374,246 A | | 12/1994 | Ray |
| 5,376,376 A | | 12/1994 | Li |
| 5,380,646 A | | 1/1995 | Knight et al. |
| 5,382,251 A | | 1/1995 | Hood et al. |
| 5,388,588 A | | 2/1995 | Nabai et al. |
| 5,394,886 A | | 3/1995 | Nabai et al. |
| 5,403,306 A | | 4/1995 | Edwards et al. |
| 5,405,402 A | | 4/1995 | Dye et al. |
| 5,409,004 A | | 4/1995 | Sloan |
| 5,444,113 A | | 8/1995 | Sinclair et al. |
| 5,451,406 A | | 9/1995 | Lawin et al. |
| 5,456,693 A | | 10/1995 | Conston et al. |
| 5,456,718 A | | 10/1995 | Szymaitis |
| 5,460,182 A | | 10/1995 | Goodman et al. |
| 5,467,780 A | | 11/1995 | Nabai et al. |
| 5,478,352 A | | 12/1995 | Fowler |
| 5,487,392 A | | 1/1996 | Haaga |
| 5,514,379 A | | 5/1996 | Weissleder et al. |
| 5,571,181 A | | 11/1996 | Li |
| 5,571,182 A | * | 11/1996 | Ersek et al. .................. 623/11 |
| 5,575,781 A | | 11/1996 | DeBusk |
| 5,628,744 A | | 5/1997 | Coleman et al. |
| 5,645,566 A | | 7/1997 | Brenneman et al. |
| 5,662,712 A | * | 9/1997 | Pathak et al. ................. 623/12 |
| 5,664,582 A | | 9/1997 | Szymaitis |
| 5,670,161 A | | 9/1997 | Healy et al. |
| 5,676,146 A | | 10/1997 | Scarborough |
| 5,707,393 A | | 1/1998 | Kensey et al. |
| 5,709,676 A | | 1/1998 | Alt |
| 5,714,551 A | | 2/1998 | Bezwada et al. |
| 5,716,407 A | | 2/1998 | Knapp et al. |
| 5,718,237 A | | 2/1998 | Haaga |
| 5,720,772 A | | 2/1998 | Eckhouse |
| 5,725,517 A | | 3/1998 | DeBusk |
| 5,752,974 A | | 5/1998 | Rhee et al. |
| 5,795,308 A | | 8/1998 | Russin |
| 5,807,276 A | | 9/1998 | Russin |
| 5,807,581 A | | 9/1998 | Rosenblatt et al. |
| 5,823,198 A | | 10/1998 | Jones et al. |
| 5,827,531 A | | 10/1998 | Morrison et al. |
| 5,853,366 A | | 12/1998 | Dowlatshahi |
| 5,856,367 A | | 1/1999 | Barrows et al. |
| 5,871,501 A | | 2/1999 | Leschinsky et al. |
| 5,871,535 A | * | 2/1999 | Wolff et al. ..................... 623/1 |
| 5,873,904 A | * | 2/1999 | Ragheb et al. .................. 623/1 |
| 5,879,357 A | | 3/1999 | Heaton et al. |
| 5,989,265 A | | 11/1999 | Bouquet De La Joliniere et al. |
| 6,006,750 A | | 12/1999 | Field |
| 6,007,495 A | | 12/1999 | Matula |
| 6,030,333 A | * | 2/2000 | Siohansi et al. ................ 600/3 |
| 6,056,700 A | * | 5/2000 | Burney et al. .............. 600/564 |
| 6,057,122 A | * | 5/2000 | Davidson .................... 435/68.1 |
| 6,068,857 A | | 5/2000 | Weitschies et al. |
| 6,071,301 A | | 6/2000 | Cragg et al. |
| 6,126,675 A | | 10/2000 | Shchervinsky et al. |
| 6,159,165 A | | 12/2000 | Ferrara et al. |
| 6,161,034 A | * | 12/2000 | Burbank et al. ............ 600/420 |
| 6,174,330 B1 | | 1/2001 | Stinson |
| 6,181,960 B1 | | 1/2001 | Jensen et al. |
| 6,183,497 B1 | | 2/2001 | Sing et al. |
| 6,200,328 B1 | | 3/2001 | Cragg et al. |
| 6,214,045 B1 | | 4/2001 | Corbitt, Jr. et al. |
| 6,228,055 B1 | | 5/2001 | Foerster et al. |
| 6,234,177 B1 | | 5/2001 | Barsch |
| 6,270,464 B1 | | 8/2001 | Fulton, III et al. |

FOREIGN PATENT DOCUMENTS

| | | |
|---|---|---|
| EP | 0 769 281 A3 | 4/1997 |
| EP | 0 769 281 A2 | 4/1997 |
| FR | 2 714 284 A1 | 6/1995 |
| WO | WO 96/08208 A1 | 3/1996 |
| WO | WO 98/47430 | 10/1998 |
| WO | WO 99/11196 | 3/1999 |
| WO | WO 99/66834 | 12/1999 |
| WO | WO 00/24320 A1 | 5/2000 |
| WO | WO 00/32253 A1 | 6/2000 |
| WO | WO 00/45854 A2 | 8/2000 |
| WO | WO 00/45858 A1 | 8/2000 |
| WO | WO 01/00101 A1 | 1/2001 |

OTHER PUBLICATIONS

Burbank, Fred and Forcier, Nancy. (1997). "Tissue Marking Clip for Stereotactic Breast Biopsy: Initial Placement Accuracy, Long–term Stability, and Usefulness as a Guide for Wire Localization," *Radiology* vol. 205 No. 2, 407–415.

Collagen Facts provided by Ajay Kumar and Biocore, Inc., 2 pages, date unknown.

Davol, Inc., *Clotting Power:* Hemostasis Products Catalog, 2 pages, website and date unknown.

Ethicon Home Page, (1998) "Ethicon: Wound Closure,"one page, (http://www.eosinc.com).

Freiherr, Greg. (1997). "Biotech Devices Promise Benefits in Wound Repair and Surgery," *Medical Device & Diagnostic Industry* Magazine, 6 pages (www.devicelink.com).

Hachisu et al., (1989). "Endoscopic Clip–Marking of Lesions Using the Newly Developed HX–3L Clip," *Surgical Endoscopy* vol. 3, 142–147.

Katz, Jon and Spera, Gabriel. (1998). "Biomaterials Research Focuses on Developing New Applications," *Medical Device & Diagnostic Industry* Magazine, 8 pages (www.devicelink.com).

Middleton, John and Tipton, Arthur. (1998). "Synthetic Biodegradable Polymers as Medical Devices," *Medical Plastics and Biomaterials* Magazine, 17 pages (www.devicelink.com).

Parker, Steve. "Steps in a Steroetactic Mammotome Biopsy," Publication by *Sally Jobe* Breast Centre, pp. 1–5, date unknown.

Publication by Medical Plastics and Biomaterials, (1997), p. 61.

Publication by Surmodics, Inc., one page, (http://www.surmodics.com), date unknown.

RaB Biochemicals, "Structure and properties of collagen," *High Quality Biochemicals from Scientist to Scientist*, 1 page, date unknown.

Storey, Robson and Wiggins, Jeffrey. (1996). "Design and Fabrication of Polyester–Fiber and Matrix Composites for Totally Absorbable Biomaterials," *Medical Plastics and Biomaterials* Magazine, 6 pages (www.devicelink.com).

Surgicel Fibrillar: Absorbable Hemostat (Oxidized Regenerated Cellulose), "Advances Hemostasis . . . Layer by Layer," Publication by Ethicon, a Johnson & Johnson company, 6 pages, date unknown.

Dufrane, P. et al. (1990). "Prebiopsy Localization of Non–Palpable Breast Cancer," *J. Belge De Radiologie* 73(5):401–404.

Lebovic, G.S. (Feb. 14–17, 2000). "Utility of a Radiolucent, Bioabsorbable Marker Following Percutaneous Excision of Breast Lesions," *University of Florida 5th Annual Multidisciplinary Breast Conference* (Poster–2 pages total).

Braverman, M.H. and Tawes, R.L. eds., (Dec. 1992). "Upjohn Gelfoam® Sterile Sponge and Sterile Powder advertisement," *Surgical Technology: International Developments in Surgery and Surgical Research* (3 pages).

Cohesion Technologies, Inc., "Business Summary," at <http://www.cohesiontech.com> (visited on Nov. 19, 1999) (3 pages).

Trovan®: Electronic Identification Systems., "Trovan Transponders," at http://www.trovan.com/transponders.htm> (visited on Dec. 13, 1999) (7 pages).

\* cited by examiner

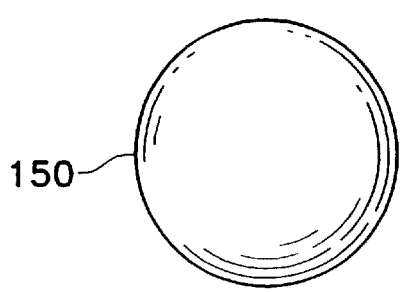
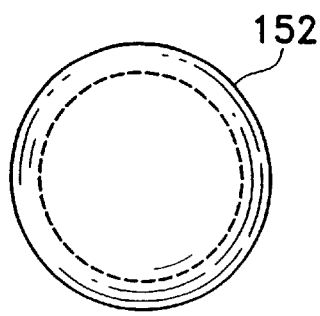
FIG. 2A        FIG. 2B
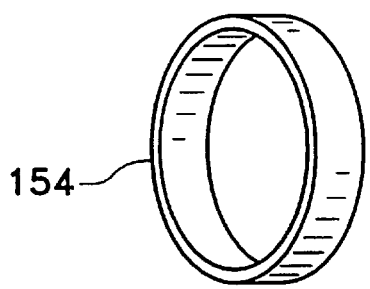
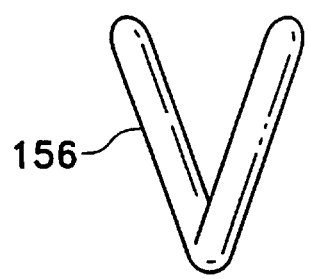
FIG. 2C        FIG. 2D
FIG. 2E
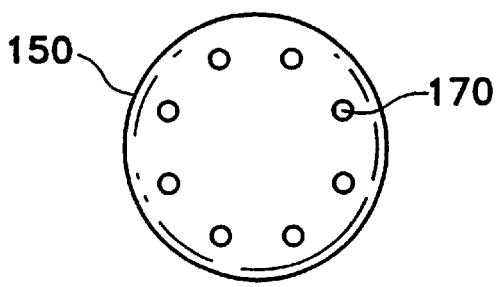
FIG. 2F

SUBCUTANEOUS CAVITY MARKING DEVICE AND METHOD

RELATED APPLICATIONS

This application is a continuation-in-part of U.S. Ser. No. 09/220,618, filed Dec. 24, 1998 now abandoned.

FIELD OF THE INVENTION

This invention is directed to subcutaneous cavity marking devices and methods. More particularly, a cavity marking device and method is disclosed that enable one to determine the location, orientation, and periphery of the cavity by radiographic, mammographic, echographic, or other non-invasive techniques. The invention typically is made up of one or more resilient bodies and a radiopaque or echogenic marker.

BACKGROUND OF THE INVENTION

Over 1.1 million breast biopsies are performed each year in the United States alone. Of these, about 80% of the lesions excised during biopsy are found to be benign while about 20% of these lesions are malignant.

In the field of breast cancer, stereotactically guided and percutaneous biopsy procedures have increased in frequency as well as in accuracy as modern imaging techniques allow the physician to locate lesions with ever-increasing precision. However, for any given biopsy procedure, a subsequent examination of the biopsy site is very often desirable. There is an important need to determine the location, most notably the center, as well as the orientation and periphery (margins) of the subcutaneous cavity from which the lesion is removed.

In those cases where the lesion is found to be benign, for example, a follow-up examination of the biopsy site is often performed to ensure the absence of any suspect tissue and the proper healing of the cavity from which the tissue was removed. This is also the case where the lesion is found to be malignant and the physician is confident that all suspect tissue was removed and the tissue in the region of the perimeter or margins of the cavity is "clean".

In some cases, however, the physician may be concerned that the initial biopsy failed to remove a sufficient amount of the lesion. Such a lesion is colloquially referred to as a "dirty lesion" or "dirty margin" and requires follow-up observation of any suspect tissue growth in the surrounding marginal area of the initial biopsy site. Thus, a re-excision of the original biopsy site must often be performed. In such a case, the perimeter of the cavity must be identified since the cavity may contain cancerous cells. Identification of the cavity perimeter necessary to avoid the risk of opening the cavity, which could release and spread cancerous cells. Moreover, the site of the re-excised procedure itself requires follow-up examination, providing further impetus for accurate identification of the location of the re-excised site. Therefore, a new marker will be placed after re-excision.

Prior methods of marking biopsy cavities utilize one or more tissue marking clips as the biopsy site marking device. Most commonly, these marker clips have a "horseshoe" configuration. The marker clips attach to the walls of the cavity when the free ends or limbs of the "horseshoe" are pinched together, trapping the tissue. This device has significant drawbacks.

For instance, prior to placing the marker clip at the cavity site, the site must be thoroughly cleaned, typically by vacuum, to remove any residual tissue debris. This minimizes the possibility that the marker clip attaches to any loose tissue as opposed to the cavity wall. Once the cavity is prepared, the clip must be examined to ensure that the limbs of the clip are substantially straight. If the limbs have been prematurely bent together, the clip will be discarded since it will most likely not attach properly to the cavity wall. Actual placement of the clip often requires additional vacuum of the cavity wall to draw the wall into the aperture between the limbs of the marking clip so that a better grip is obtained between the limbs of the clip. Additionally, there is always the possibility that the clip may detach from the cavity wall during or after withdrawal of the tools used to place the clip into the cavity.

Aside from the problems inherent in the placement of the marking clip, there are also limitations associated with how well the marking clip can identify a biopsy cavity. As the marking clip must trap tissue for proper attachment, in cases of endoscopic placement, the clip can only be placed on a wall of the cavity substantially opposite to the opening of the cavity.

Moreover, patient concern limits the number of clips that may be placed in a cavity. As a result, the medical practitioner is forced to identify the outline of a three dimensional cavity by a single point as defined by the marking clip. Obviously, determination of the periphery of a biopsy cavity from one point of the periphery is not possible.

These limitations are compounded as the biopsy cavity fills within a few hours with bodily fluids, which eventually renders the cavity invisible to non-invasive techniques. Another difficulty in viewing the clip stems from the fact that the clip is attached to the side, not the center, of the cavity. This makes determining the spatial orientation and position of the cavity difficult if not impossible during follow-up examination. Additionally, during a stereotactic breast biopsy procedure, the breast is under compression when the marking clip is placed. Upon release of the compressive force, determining the location of the clip can be unpredictable, and the orientation as well as the location of the periphery of the cavity are lost.

The marker clip does not aid in the healing process of the biopsy wound. Complications may arise if the marker strays from its original placement site. As described above, if a re-excision of the site is required, the marker clip may also interfere when excision of a target lesion is sought.

Other devices pertaining to biopsy aids are directed to assisting in the healing and closure of the biopsy wound; thus they do not aid the clinical need or desirability of accurately preserving the location and orientation of the biopsy cavity. See, e.g., U.S. Pat. Nos. 4,347,234, 5,388,588, 5,326,350, 5,394,886, 5,467,780, 5,571,181, and 5,676,146.

SUMMARY OF THE INVENTION

This invention relates to devices and procedures for percutaneously marking a biopsy cavity. In particular, the inventive device is a biopsy cavity-marking body made of a resilient, preferably bioabsorbable material having at least one preferably radiopaque or echogenic marker. The device may take on a variety of shapes and sizes tailored for the specific biopsy cavity to be filled. For example, the device in its simplest form is a spherical or cylindrical collagen sponge having a single radiopaque or echogenic marker located in its geometric center. Alternatively, the body may have multiple components linked together with multiple radiopaque or echogenic markers.

A further aspect of the invention allows the marker or the body, singly or in combination, to be constructed to have a varying rate of degradation or bioabsorption. For instance, the body may be constructed to have a layer of bioabsorbable material as an outer "shell." Accordingly, prior to degradation of the shell, the body is palpable. Upon degradation of the shell, the remainder of the body would degrade at an accelerated rate in comparison to the outer shell.

The device may additionally contain a variety of drugs, such as hemostatic agents, pain-killing substances, or even healing or therapeutic agents that may be delivered directly to the biopsy cavity. Importantly, the device is capable of accurately marking a specific location, such as the center, of the biopsy cavity, and providing other information about the patient or the particular biopsy or device deployed.

The device is preferably, although not necessarily, delivered immediately after removal of the tissue specimen using the same device used to remove the tissue specimen itself Such devices are described in pending U.S. patent application Ser. No. 09/145,487 (Attorney Docket No. 41269-20002.00), filed Sep. 1, 1998 and entitled "PERCUTANEOUS TISSUE REMOVAL DEVICE", and pending U.S. patent application Ser. No. 09/184,766 (Attorney Docket No. 41269-20001.20), filed Nov. 2, 1998 and entitled "EXPANDABLE RING PERCUTANEOUS TISSUE REMOVAL DEVICE" the entirety of each are which hereby incorporated by reference. The device is compressed and loaded into the access device and percutaneously advanced to the biopsy site where, upon exiting from the access device, it expands to substantially fill the cavity of the biopsy. Follow-up noninvasive detection techniques, such as x-ray mammography or ultrasound may then be used by the physician to identify, locate, and monitor the biopsy cavity site over a preferred period of time.

The device is usually inserted into the body either surgically via an opening in the body cavity, or through a minimally invasive procedure using such devices as a catheter, introducer or similar type device. When inserted via the minimally invasive procedure, the resiliency of the body allows the device to be compressed upon placement in a delivery device. Upon insertion of the cavity marking device into the cavity, the resiliency of the body causes the cavity marking device to self-expand, substantially filling the cavity. The resiliency of the body can be further predetermined so that the body is palpable, thus allowing tactile location by a surgeon in subsequent follow-up examinations. Typically, the filler body is required to be palpable for approximately 3 months. However, this period may be increased or decreased as needed.

The expansion of the resilient body can be aided by the addition of a bio-compatible fluid which is absorbed into the body. For instance, the fluid can be a saline solution, a painkilling substance, a healing agent, a therapeutic fluid, or any combination of such fluids. The fluid or combination of fluids may be added to and absorbed by the body of the device before or after deployment of the device into a cavity. For example, the body of the device may be pre-soaked with the fluid and then delivered into the cavity. In this instance, the fluid aids the expansion of the body of the device upon deployment. Another example is provided as the device is delivered into the cavity without being pre-soaked. In such a case, fluid is delivered into the cavity after the body of the device is deployed into the cavity. Upon delivery of the fluid, the body of the device soaks the fluid, thereby aiding the expansion of the cavity marking device as it expands to fit the cavity. The fluid may be, but is not limited to being, delivered by the access device.

By "bio-compatible fluid" what is meant is a liquid, solution, or suspension that may contain inorganic or organic material. For instance, the bio-compatible fluid is preferably saline solution, but may be water or contain adjuvants such as medications to prevent infection, reduce pain, or the like. Obviously, the liquid is intended to be a type that does no harm to the body.

After placement of the cavity marking device into the cavity, the bioabsorbable body degrades at a predetermined rate. As the body of the cavity marking device is absorbed, tissue is substituted for the bioabsorbable material. Moreover, while the body degrades, the marker, which is usually suspended substantially in the volumetric center of the body of the device, is left in the center of the cavity. Thus, during a subsequent examination, a medical practitioner having knowledge of the dimensions of the body of the cavity marking device can determine the location as well as the periphery of the biopsy cavity. The orientation of the cavity is self-evident as the marker is left in substantially the center of the cavity. For the case where multiple markers are used, the markers are usually placed in a manner showing directionality.

Both the body and the marker can be made, via radiopaque or echogenic coatings or in situ, to degrade and absorb into the patient's body over a predetermined period of time. It is generally preferred that if the marker's radiopacity or echogenicity is chosen to degrade over time, such degradation does not take place within at least one year after implantation of the inventive device. In this way, if a new lump or calcification (in the case of a breast biopsy) is discovered after the biopsy, such a marker will allow the physician to know the relation of such new growth in relation to the region of excised tissue. On the other hand, and as discussed below, a bioabsorption period of three months is preferred for any such coatings on the perimeter of the body itself.

This invention further includes the act of filling the biopsy cavity with a bioabsorbable liquid, aerosol or gelatinous material, preferably gelatinous collagen, allowing the material to partially solidify or gel and then placing a marker, which may have a configuration as described above, into the center of the bioabsorbable material. The gel may also be made radiopaque or echogenic by the addition of radiopaque materials, such as barium- or bismuth-containing compounds and the like, as well as particulate radio-opaque fillers, e.g., powdered tantalum or tungsten, barium carbonate, bismuth oxide, barium sulfate, to the gel.

This method may be combined with any aspect of the previously described devices as needed. For instance, one could insert a hemostatic or pain-killing substance as described above into the biopsy cavity along with the bioabsorbable material. Alternatively, a bioabsorbable marker could be inserted into a predetermined location, such as the center, of the body of bioabsorbable material.

It is within the scope of this invention that either or both of the marker or markers and the bioabsorbable body may be radioactive, if a regimen of treatment using radioactivity is contemplated.

This procedure may be used in any internal, preferably soft, tissue, but is most useful in breast tissue, lung tissue, prostate tissue, lymph gland tissue, etc. Obviously, though, treatment and diagnosis of breast tissue problems forms the central theme of the invention.

In contrast to the marker clips as described above, the cavity marking device has the obvious advantage of marking the geometric center of a biopsy cavity. Also, unlike the marking clip which has the potential of attaching to loose tissue and moving after initial placement, the marking device self-expands upon insertion into the cavity, thus providing resistance against the walls of the cavity thereby anchoring itself within the cavity. The marking device may be configured to be substantially smaller, larger, or equal to the size of the cavity, however, in some cases the device will be configured to be larger than the cavity. This aspect of the biopsy marking device provides a cosmetic benefit to the patient, especially when the biopsy is taken from the breast. For example, the resistance provided by the cavity marking device against the walls of the cavity may minimize any "dimpling" effect observed in the skin when large pieces of tissue are removed, as, for example, during excisional biopsies.

Although the subcutaneous cavity marking device and method described above are suited for percutaneous placement of the marker within a biopsy cavity it is not intended that the invention is limited to such placement. The device and method are also appropriate for intra-operative or surgical placement of the marker within a biopsy cavity.

BRIEF DESCRIPTION OF THE DRAWINGS

FIGS. 2A–2F illustrate various configurations of the marker.

DETAILED DESCRIPTION OF THE INVENTION

Figure 1A:
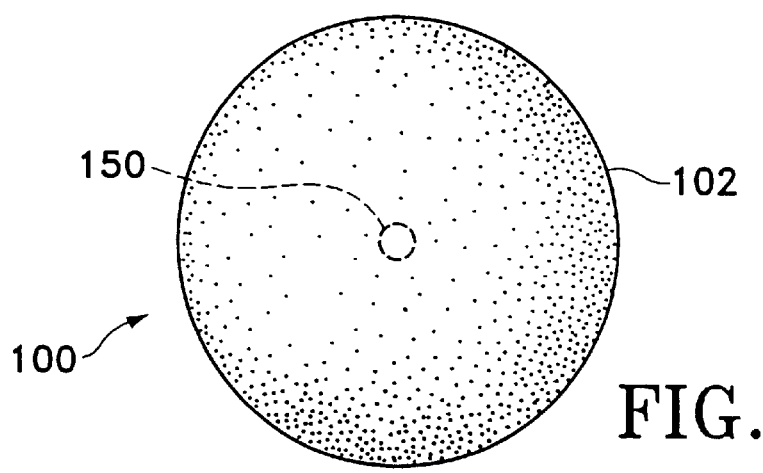
FIG. 1A illustrates a tissue cavity marking device with a spherical body and a single centrally-located marker.
Figure 1B:
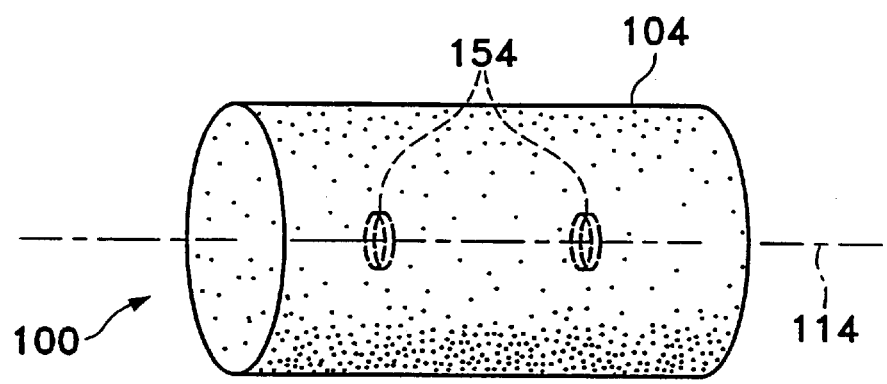
FIG. 1B shows a tissue cavity marking device with a cylindrical body and two ring-shaped markers aligned near the cylinder's longitudinal axis.
Figure 1C:
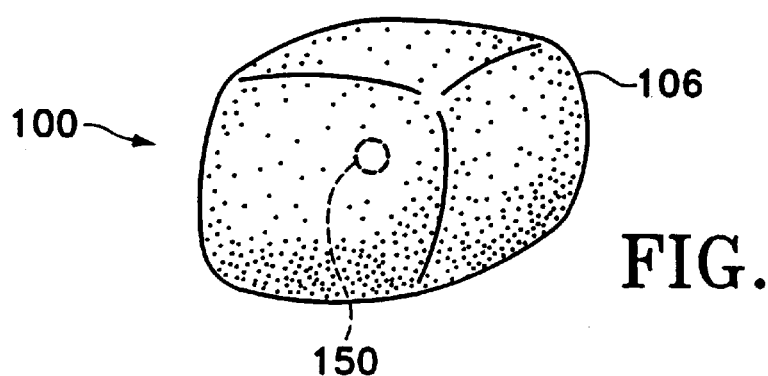
FIG. 1C shows another tissue cavity marking device with a multi-faced or irregular body and a single centrally-located marker.

FIGS. 1A–1C show various configurations of a preferred subcutaneous cavity marking device of the present invention. Here the marking device (100) is displayed as having either a generally spherical body (102) (FIG. 1A), a generally cylindrical body (104) (FIG. 1B), or a multi-faced or irregular body (106) (FIG. 1C). In general, it is within the scope of this invention for the body to assume a variety of shapes. For example, the body may be constructed to have substantially curved surfaces, such as the preferred spherical (102) and cylindrical (104) bodies of FIGS. 1A and 1B, respectively. The body may have conical or ellipsoidal, etc. shapes as well. It is further within the scope of this invention for the body to have substantially planar surfaces, such as polyhedric (i.e. cubic, tetrahedral, etc.) or prismatic, etc. forms. Finally, the body may also have an irregular or random shape, in the case of a gel, combining features of various curved and planar surfaces. Body (106) of FIG. 1C is an example of such an irregular body shape. The particular body shape will be chosen to best match to the biopsy cavity in which the device is placed. However, it is also contemplated that the body shape can be chosen to be considerably larger than the cavity. Therefore, expansion of the device will provide a significant resistance against the walls of the cavity. Moreover, the aspect ratio of the device is not limited to what is displayed in the figures. For example, the cylindrical body (104) may have a shorter or longer length as required.

In the bodies of FIGS, 1A and 1C, the generally spherical marker (150) is located at or near the geometric center of the body. Such a configuration will aid the physician in determining the exact location of the biopsy cavity, even after the body degrades and is absorbed into the human or mammalian body.

In the case of the ring-shaped markers (154) of FIG. 1B, they are generally aligned along the longitudinal axis (114) of body (104). Note that although the ring-shaped markers (154) are spatially oriented so that the longitudinal axis (114) of the body (104) lies along the longitudinal axes (not shown) of each marker (154), each marker may individually or together assume a wide variety of random or predetermined spatial orientations other than the aligned orientation as seen in FIG. 1C. It can be appreciated that any asymmetric marker such as marker (154) is useful in aiding a physician to determine the spatial orientation of the deployed inventive device.

Obviously, marker (150), (154) may reside in locations other than those demonstrated in FIGS, 1A–1C. It is, however, preferred that markers (150), (154) dwell in a predetermined, preferably central, location and orientation in the device body so to aid the physician in determining the location and orientation of the biopsy cavity. The markers herein described may be affixed to the interior or on the surface of the body by any number of suitable methods. For instance, the marker may be merely suspended in the interior of the body (especially in the case where the body is a gel), it may be woven into the body (especially in the case where the marker is a wire or suture), it may be press fit onto the body (especially in the case where the marker is a ring or band), or it may affixed to the body by a biocompatible adhesive. Any suitable means to affix or suspend the marker into the body in the preferred location is within the scope of the present invention.

Figure 1D:
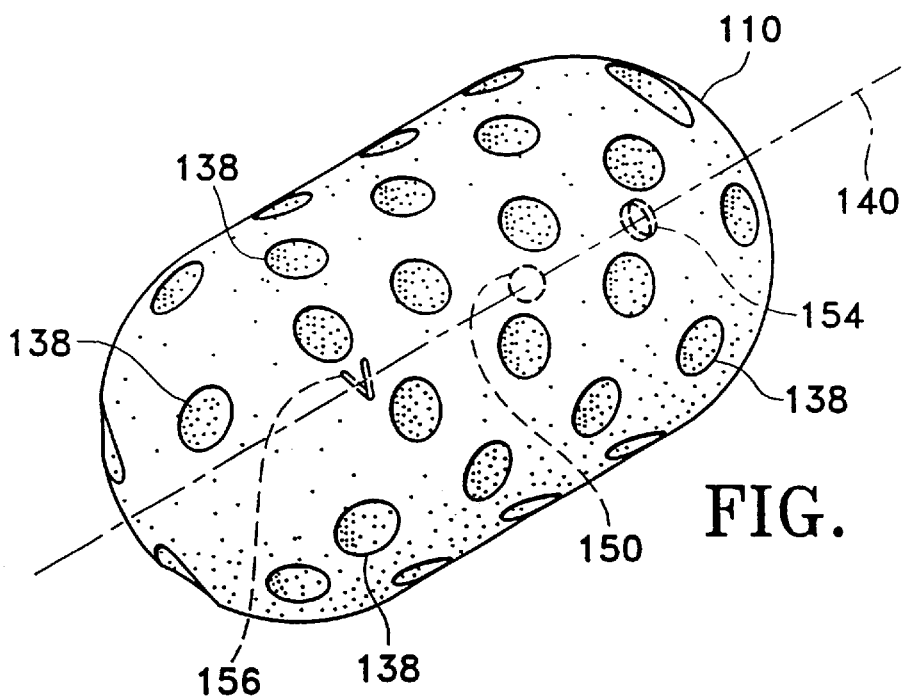
FIG. 1D illustrates a tissue cavity marking device with a body having pores.
Figure 1E:
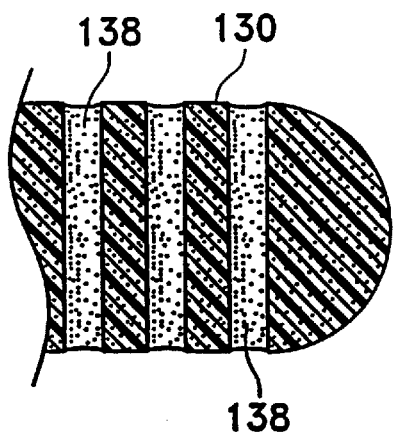
FIG. 1E is a partial cross-sectional view of FIG. 1D.

Tissue regrowth in a particular orientation can also be promoted by a body design shown in FIG. 1D. Here, body (110) contains a number of pores (138) through which tissue may grow. The pores may also be aligned in a substantially parallel fashion, traversing the thickness of the body so that tissue may regrow from one side of the body through to the other side. This is demonstrated in inset FIG. 1E, which shows a portion (130) of FIG. 1D in partial longitudinal cross section, complete with pores (138) traversing through the thickness of portion (130). Such pores (138) can be parallel to each other as shown in FIG. 1E, or they may be perpendicularly, radially, or even randomly oriented in the device body.

A trio of markers is also shown in FIG. 1D evenly aligned along the body longitudinal axis (140). Barb marker (156), spherical marker (150), and ring-shaped marker (154) demonstrate the use of different multiple markers in a single body (110). As previously described, such a design helps a physician to determine the spatial orientation of the inventive device when it is deployed in a biopsy cavity. Although the barb marker (156) is illustrated in a 'V' configuration, it is an important aspect of the barb marker (156) to have a shape that is clearly not spherical. This allows the barb marker (156) to be easily distinguished from calcifications that may be observed during any non-invasive imaging techniques.

Figure 1F:
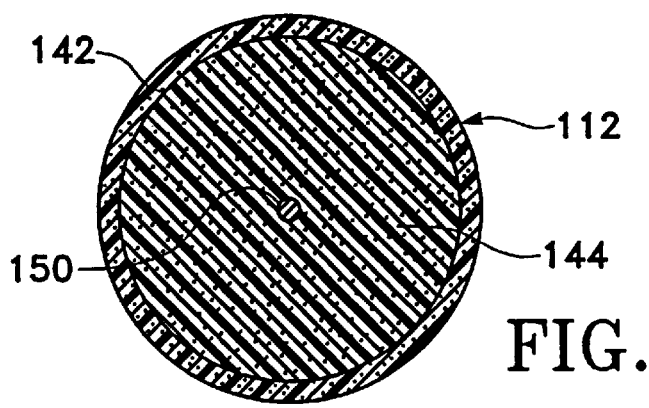
FIG. 1F illustrates a tissue cavity marking device with a body having an outer shell of a bioabsorbable material.

FIG. 1F depicts a further embodiment of the present invention in which body (112) is enveloped in a outer shell (142) consisting of a layer of bioabsorbable material such those mentioned above. This configuration allows the perimeter of the biopsy cavity to be marked to avoid exposing the cavity, in the case of a "dirty" margin where re-excision may be necessary, to remaining cancerous cells as the tissue begins to re-grow into the cavity. Such a shell (142) can be radiopaque and/or echogenic in situ, or it may be augmented with an additional coating of an echogenic and/or radiopaque material. The shell (142) can also be made to be palpable so that the physician or patient can be further aided in determining the location and integrity of the implanted inventive device.

Shell (142) may be designed to have a varying bioabsorption rate depending upon the thickness and type of material making up the shell (142). In general, the shell can be designed to degrade over a period ranging from as long as a year or more to as little as several months, weeks, or even days. It is preferred that such a bioabsorbable shell be designed to degrade between two and six months; especially preferred is three months. In the design of FIG. 1F, interior (144) of body (112) may be a cross-linked, collagenous material that is readily absorbed by the human or mammalian body once the shell (142) degrades. Interior (144) may be filled with a solid or gelatinous material that can be optionally made radiopaque by any number of techniques herein described.

As will be described in additional detail with respect to FIGS. 2A–2F, marker (150) in the device shown in FIG. 1F may be permanently radiopaque or echogenic, or it also may be bioabsorbable and optionally coated with a radiopaque and/or echogenic coating that similarly degrades over a predetermined period of time. It is more important from a clinical standpoint that the marker remain detectable either permanently or, if the patient is uncomfortable with such a scenario, for at least a period of about one to five years so that the physician may follow up with the patient to ensure the health of the tissue in the vicinity of the biopsy cavity. Especially preferable is a marker whose radiopacity or echogenicity lasts from between about one and three years.

Each of the bodies depicted in FIGS. 1A–1E may be made from a wide variety of solid, liquid, aerosol-spray, spongy, or expanding gelatinous bioabsorbable materials such as collagen, cross-linked collagen, regenerated cellulose, synthetic polymers, synthetic proteins, and combinations thereof. Also contemplated is a body made from a fibrin-collagen matrix, which further prevent unnecessary bleeding, and minimizes the possibility of hematoma formation.

Examples of synthetic bioabsorbable polymers that may be used for the body of the device are polyglycolide, or polyglycolic acid (PGA), polylactide, or polylactic acid (PLA), poly $\epsilon$-caprolactone, polydioxanone, polylactide-co-glycolide, e.g., block or random copolymers of PGA and PLA, and other commercial bioabsorbable medical polymers. Preferred is spongy collagen or cellulose. As mentioned above, materials such as hemostatic and pain-killing substances may be incorporated into the body and marker of the cavity marking device. The use of hemostasis-promoting agents provides an obvious benefit as the device not only marks the site of the biopsy cavity but it aids in healing the cavity as well. Furthermore, such agents help to avoid hematomas. These hemostatic agents may include AVITENE Microfibrillar Collagen Hemostat, ACTIFOAM collagen sponge, sold by C. R. Bard Inc., GELFOAM, manufactured by Upjohn Company, SURGICEL Fibrillar from Ethicon Endosurgeries, Inc., and TISSEEL VH, a surgical fibrin sealant sold by Baxter Healthcare Corp. The device may also be made to emit therapeutic radiation to preferentially treat any suspect tissue remaining in or around the margin of the biopsy cavity. It is envisioned that the marker would be the best vehicle for dispensing such local radiation treatment or similar therapy. Also, the body itself may be adapted to have radiopaque, echogenic, or other characteristics that allow the body to be located by non-invasive technique without the use of a marker. Such characteristics permit the possibility of locating and substantially identifying the cavity periphery after deployment but prior to absorption of the device. Furthermore, an echogenic coating may be placed over the radiopaque marker to increase the accuracy of locating the marker during ultrasound imaging.

FIGS. 2A–2F illustrate various forms of the marker (110). The marker (110) may be in the form of a sphere (150) (FIG. 2A), a hollow sphere (152) (FIG. 2B), a ring or band (154) (FIG. 2C), a barb (156) (FIG. 2D), or a flexible suture or flexible wire (158) (FIG. 2E). Also, the marker may have a distinguishing mark (170) (FIG. 2F). As mentioned above, the barb (156) is illustrated in FIG. 2D as having a "V" shape. The barb (156) is intended to distinguish the marker from calcifications when viewed under non-invasive imaging techniques. As such, the barb (156) is not limited to the "V" shape, rather it has a shape that is easily distinguishable from a spherical or oval calcification.

The hollow sphere (152) marker design of FIG. 2B is more susceptible to detection by ultrasound than the solid sphere (150) of FIG. 2A. Such sphere markers (150, 152) can be a silicon bead, for instance. In the case of a ring or band marker (154) seen in FIG. 2C, the body of the cavity marking device may be woven or placed through the band/ring (154). The marker may also be a wire or suture (158) as shown in FIG. 2E and as discussed in greater detail below. In such a case, the marker (158) may be affixed to the exterior perimeter of the body by an adhesive or woven through the body. Another improvement may arise from the marker wire or suture (158) being configured in a particular pattern within the body of the device, e.g., wrapping around the body in a helical manner. Further, the suture or wire marker can be deployed as a loosely wound ball or mass of suture that when deployed into a tissue cavity, fills the cavity. The suture or wire can also looped through the band/ring (154); in this configuration (not shown), the suture or wire can also act as the body of the inventive device. The suture or wire (158) is flexible to facilitate the expansion of the body while in the cavity. In the case of the marker (150) shown in FIG. 2F, distinguishing or identifying mark (170) can be in the form of simple marks as shown, or it may be one or more numbers, letters, symbols, or combinations thereof. These marks (170) are preferably located in more than one location on the marker (150) so that the marker may be readily and simply identified from multiple orientations under a variety of viewing conditions. Such a mark (170) can be used to identify the patient and her condition, provide information about the marker and body of the tissue cavity marking device, provide information about the circumstances and date of the implantation, who performed the procedure, where the procedure was performed, etc. In the case of multiple biopsy sites, this distinguishing mark (170) permits one to differentiate and identify each different site. The mark (170) may be applied via any number of techniques such as physical inscription, physical or plasma deposition, casting, adhesives, etc. The mark (170) may also be an electronic chip providing any necessary information in electronic form that can be remotely detected by appropriate means.

An important aspect of the invention is that the marker may be radiopaque, echogenic, mammographic, etc. so that it can be located by non-invasive techniques. Such a feature can be an inherent property of the material used for the marker. Alternatively, a coating or the like can be added to the marker to render the marker detectable or to enhance its detectability. For radiopacity, the marker may be made of a non-bioabsorbable radiopaque material such as platinum, platinum-iridium, platinum-nickel, platinum-tungsten, gold, silver, rhodium, tungsten, tantalum, titanium, nickel, nickel-titanium, their alloys, and stainless steel or any combination of these metals. By mammographic we mean that the component described is visible under radiography or any other traditional or advanced mammography technique in which breast tissue is imaged.

As previously discussed, the marker can alternatively be made of or coated with a bioabsorbable material. In this case, the marker can, for instance, be made from an additive-loaded polymer. The additive is a radiopaque, echogenic, or other type of substance that allows for the non-invasive detection of the marker. In the case of radiopaque additives, elements such as barium- and bismuth-containing compounds, as well as particulate radio-opaque fillers, e.g., powdered tantalum or tungsten, barium carbonate, bismuth oxide, barium sulfate, etc. are preferred. To aid in detection by ultrasound or similar imaging techniques, any component of the device may be combined with an echogenic coating. One such coating is ECHO-COAT from STS Biopolymers. Such coatings contain echogenic features which provide the coated item with an acoustically reflective interface and a large acoustical impedance differential. As stated above, an echogenic coating may be placed over a radiopaque marker to increase the accuracy of locating the marker during ultrasound imaging.

Note that the radiopacity and echogenicity described herein for the marker and the body are not mutually exclusive. It is within the scope of the present invention for the marker or the body to be radiopaque but not necessarily echogenic, and for the marker or the body to be echogenic but not necessarily radiopaque. It is also within the scope of the invention that the marker and the body are both capable of being simultaneously radiopaque and echogenic. For example, if a platinum ring marker were coated with an echogenic coating, such a marker would be readily visible under x-ray and ultrasonic energy. A similar configuration can be envisioned for the body or for a body coating.

The marker is preferably large enough to be readily visible to the physician under x-ray or ultrasonic viewing, for example, yet be small enough to be able to be percutaneously deployed into the biopsy cavity and to not cause any difficulties with the patient. More specifically, the marker will not be large enough to be palpable or felt by the patient.

Figure 3A:
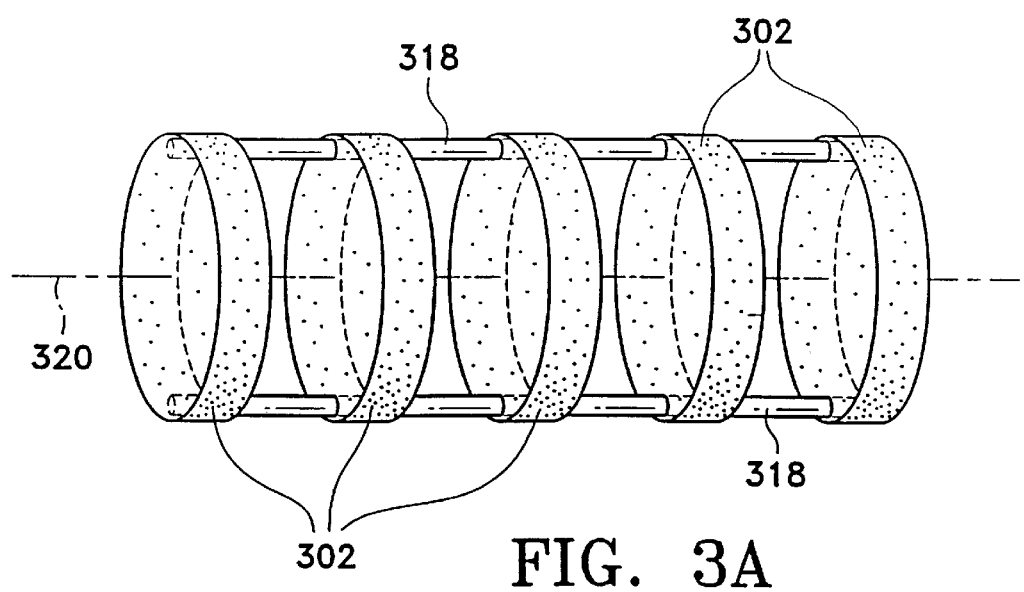
FIG. 3A illustrates a cavity marking device having multiple body components traversed by a single wire or suture marker, or multiple wires or suture markers.

Another useful version of the invention is shown in FIG. 3A. In this device, there are several cylindrical body members (302); however, there is no limit to the number of body members that can make up the device. The body members (302) can individually or together take on a variety of sizes and shapes as discussed above depending on the characteristics of the biopsy cavity to be filled. The body members (302) may uniformly or in combination be made of one or more materials suitable for use in a biopsy cavity as previously described.

Here one or more markers may traverse two or more body member segments through the interior of the body members (302) as shown in FIG. 3A. Here, markers (318) are located substantially parallel to the longitudinal axis (320) of each right cylindrical body member (302) in their interior, connecting each body member (302) while marking their geometric center as between the markers. Such a marker (318) may be used in conjunction with the other markers as described above and may also be accompanied by one or more additional markers arranged randomly or in a predetermined pattern to variously mark particular sections of the device. Alternately, such a marker may, singly or in combination with other markers, be affixed on or near the surface of the sponge so as to mark the perimeter of the body member (302).

Of course, when used in conjunction with other connecting markers, marker (318) need not necessarily connect each body member; it may be used solely to indicate the orientation or location of each individual sponge or the entire device, depending on the material, geometry, size, orientation, etc. of marker (318). When not used in this connecting function, therefore, marker (318) need not traverse two body members (302) as shown in FIG. 3A.

Figure 3B:
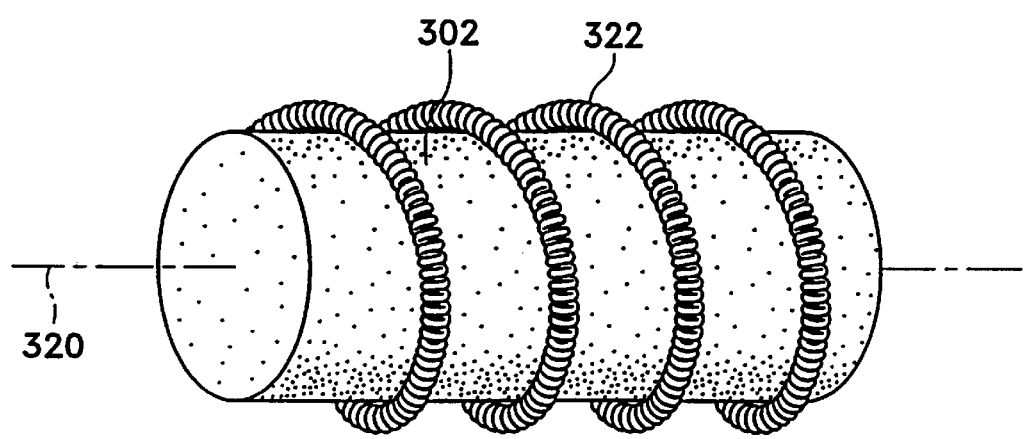
FIG. 3B illustrates a cavity marking device having a helically wound wire or suture marker.
Figure 3C:
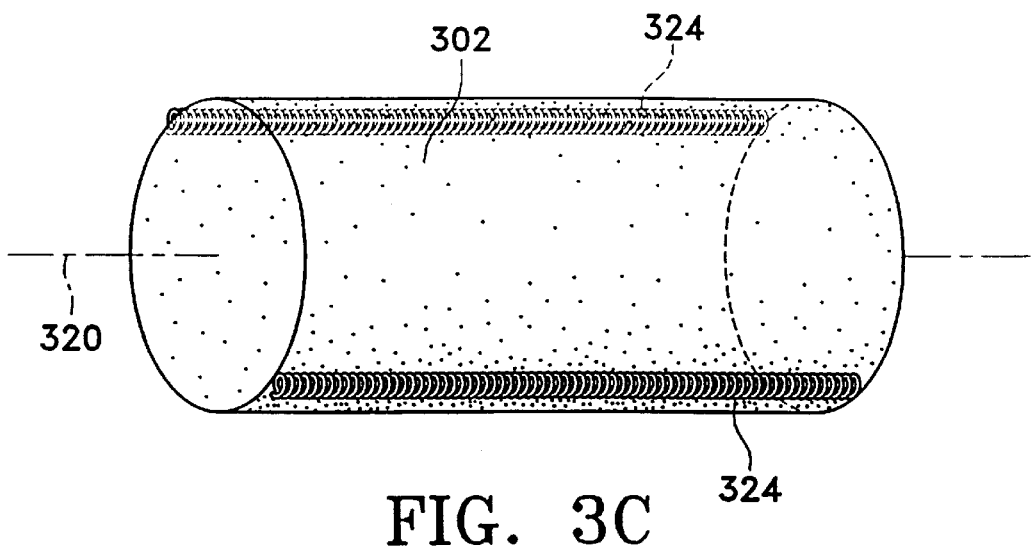
FIG. 3C illustrates a cavity marking device having wire or suture markers on the perimeter of the body.
Figure 3D:
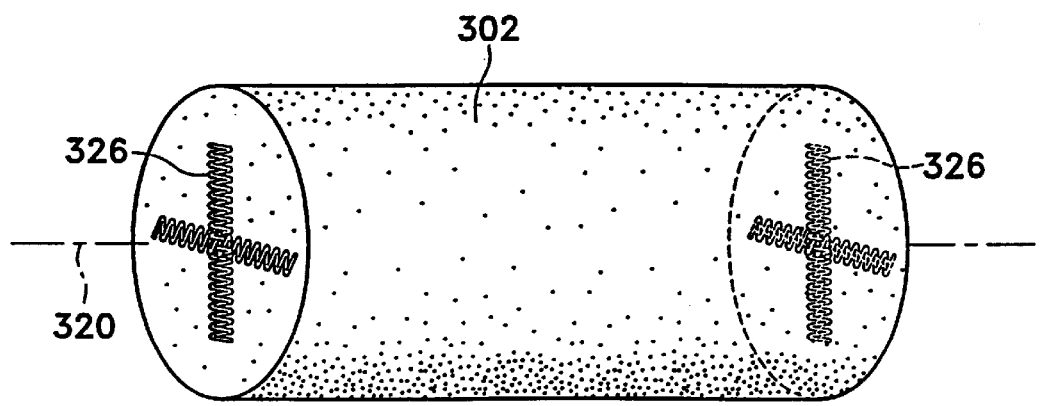
FIG. 3D illustrates a cavity marking device having wire or markers on the ends of the body.

A variety of patterns can be envisioned in which all or part of the perimeter of the sponge body is marked. For example, a marker (322) can wrap around the body (302) in a helical pattern (FIG. 3B), or it can be used in conjunction with other markers (324) in a pattern parallel to the longitudinal axis (320) of the body (FIG. 3C). Another useful perimeter marking pattern is shown in FIG. 3D, where marker segments (326) are affixed at or near the surface of the circular bases of the cylindrical body (302) in a cross pattern, indicating the ends of the sponge and their center. As seen form the figures, the markers(s) may, but do not necessarily, have some texture. Any marker pattern, internal or external to the body, is within the scope of the present invention. For the applications depicted in FIGS. 3A–3D, it is preferred that the marker be a radiopaque or echogenic wire or suture.

Another possible configuration is obtained by combining the suture or wire markers (158) in a body with any other type marker (150, 152, 154, or 156) or vice versa. For example, in FIG. 3B, a spherical marker (150) may be placed in the center of the cylindrical body (302.) Therefore, the cylindrical body (302) would contain the suture or wire marker (322) wrapped helically adjacent to the outer perimeter, and a marker (150) would be placed in the center of the cylindrical body (302). Such a combination may be obtained with any of the body and marker configurations as defined above.

Also, turning back to the marking device (100) in FIG. 1A or the marking device (100) of FIG. 1B, the markers (150 or 154) may be substituted with one or more suture or wire markers (158) preferably, but not exclusively, extending through the center and pointing radially away from the center. This configuration allows marking of the cavity perimeter and establishing of the directionality of the cavity itself.

Any of the previously-described additional features of the inventive device, such as presence of pain-killing or hemostatic drugs, the capacity for the marker to emit therapeutic radiation for the treatment of various cancers, the various materials that may make up the marker and body, as well as their size, shape, orientation, geometry, etc. may be incorporated into the device described above in conjunction with FIGS. 3A–3D.

Figure 4A:
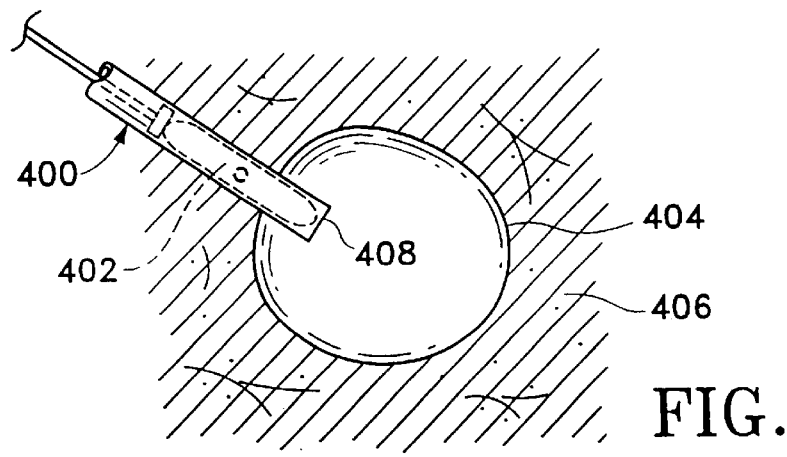
FIGS. 4A–4C illustrate a method of marking a biopsy tissue cavity with the device of the present invention.
Figure 4B:
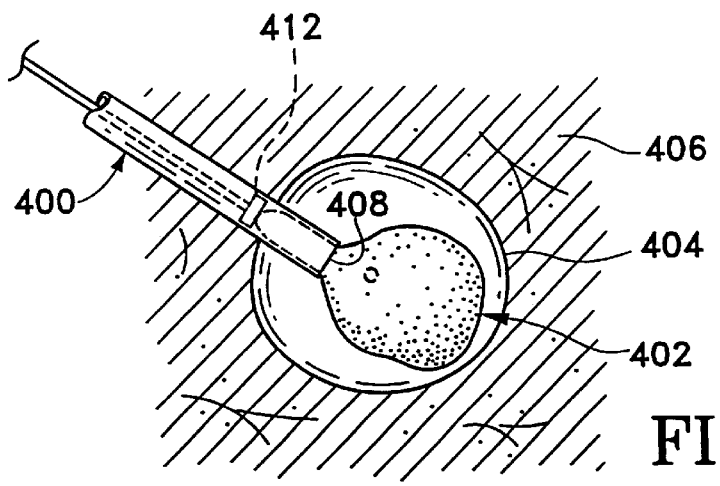
Figure 4C:
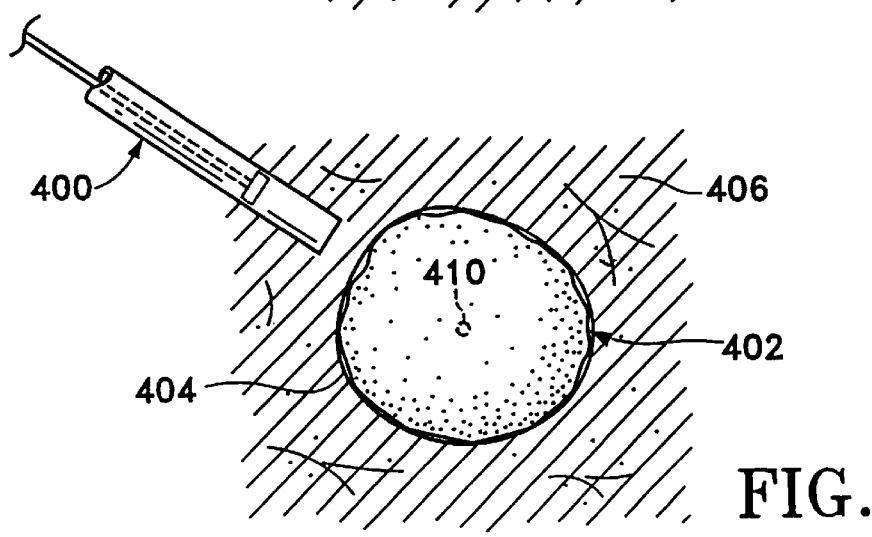

Turning now to FIGS. 4A–4C, a method of delivering the inventive device of FIG. 1A is shown. FIG. 4A details the marking device (402) just prior to delivery into a tissue cavity (404) of human or other mammalian tissue, preferably breast tissue (406). As can be seen, the step illustrated in FIG. 4A shows a suitable tubular percutaneous access device (400), such as a catheter or delivery tube, with a distal end (408) disposed in the interior of cavity (404). As previously described, the marking device (402) may be delivered percutaneously through the same access device (400) used to perform the biopsy in which tissue was removed from cavity (404). Although this is not necessary, it is less traumatic to the patient and allows more precise placement of the marking device (402) before fluid begins to fill the cavity (400).

In FIG. 4B, marking device (402) is shown being pushed out of the distal end (408) of access device (400) by a pusher (412) and resiliently expanding to substantially fill the tissue cavity (404).

Finally, in FIG. 4C, access device (400) is withdrawn from the breast tissue, leaving marking device (402) deployed to substantially fill the entire cavity (404) with radiopaque or echogenic marker (410) suspended in the geometric center of the marking device (402) and the cavity (404). As mentioned above, the marking device (402) may be sized to be larger than the cavity (404) thus providing a significant resistance against the walls of the cavity (404).

Figure 4D:
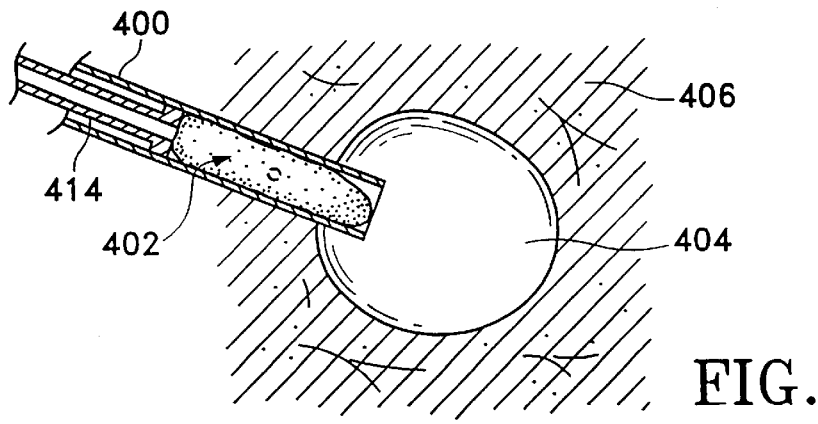
FIGS. 4D–4F illustrate a method of marking a biopsy tissue cavity with the device of the present invention wherein a bio-compatible fluid is delivered to the cavity marking device after placement.
Figure 4E:
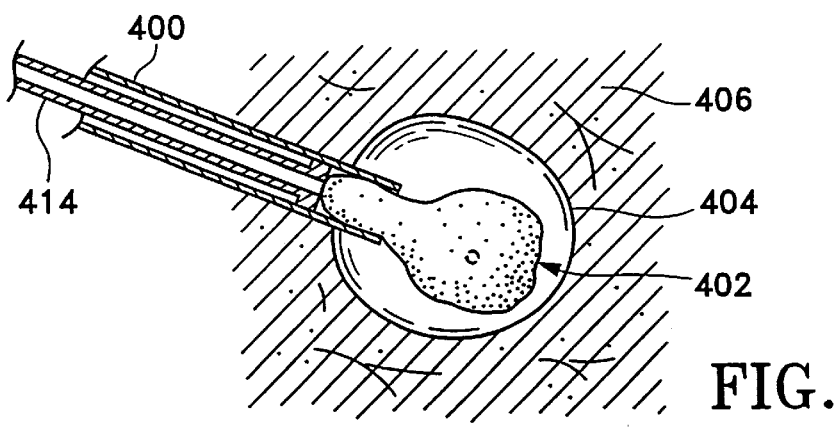
Figure 4F:
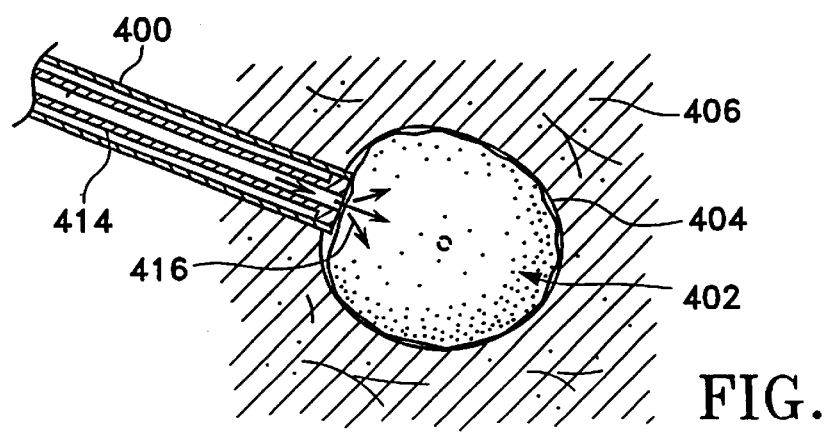

FIGS. 4D–4F show a method of delivering the marking device (402) into a tissue cavity (404) by a plunger (414) that is capable of both advancing the marking device (402) and delivering a bio-compatible fluid (416). The "bio-compatible fluid" is a liquid, solution, or suspension that may contain inorganic or organic material. The fluid (416) is preferably a saline solution, but may be water or contain adjuvants such as medications to prevent infection, reduce pain, or the like. Obviously, the fluid (416) is intended to be a type that does no harm to the body.

FIG. 4D details the marking device (402) prior to delivery into the tissue cavity (404). In FIG. 4E, a plunger (414) pushes the marking device (402) out of the access device (400). Upon exiting the ac cess device (400) the marking device (402) begins resiliently expanding to substantially fill the cavity (404).

FIG. 4F shows the plunger (414) delivering the bio-compatible fluid (416) into the cavity (404). The fluid (416) aids the marking device (402) in expanding to substantially fill the cavity (404). In this example, the bio-compatible fluid (416) is delivered subsequent to the placement of the marking device (402) in the cavity (404). The marking device (402) may also be soaked with fluid (416) prior to placement in the cavity (404).

Figure 4G:
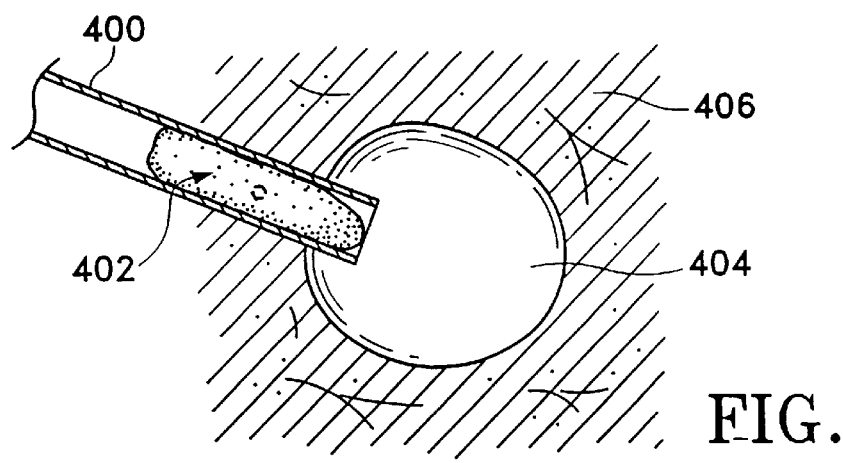
FIGS. 4G–4I illustrate a method of marking a biopsy tissue cavity with the device of the present invention wherein a bio-compatible fluid is used to push the cavity marking device out of the access device and into the biopsy tissue cavity.
Figure 4H:
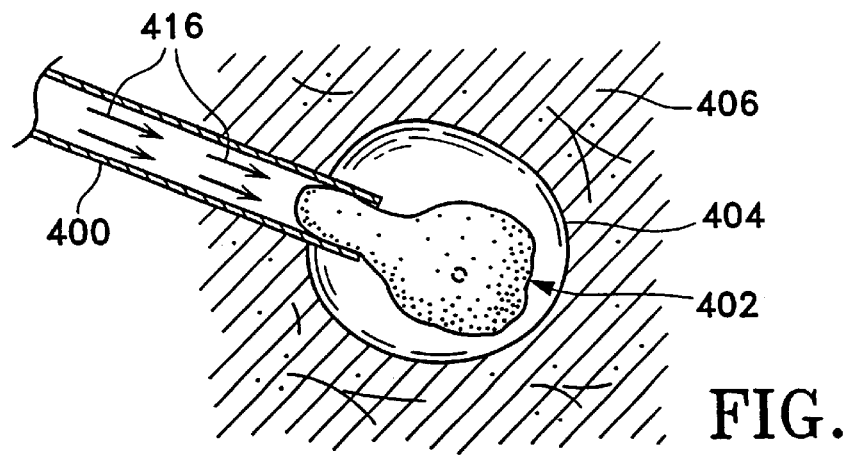
Figure 4I:
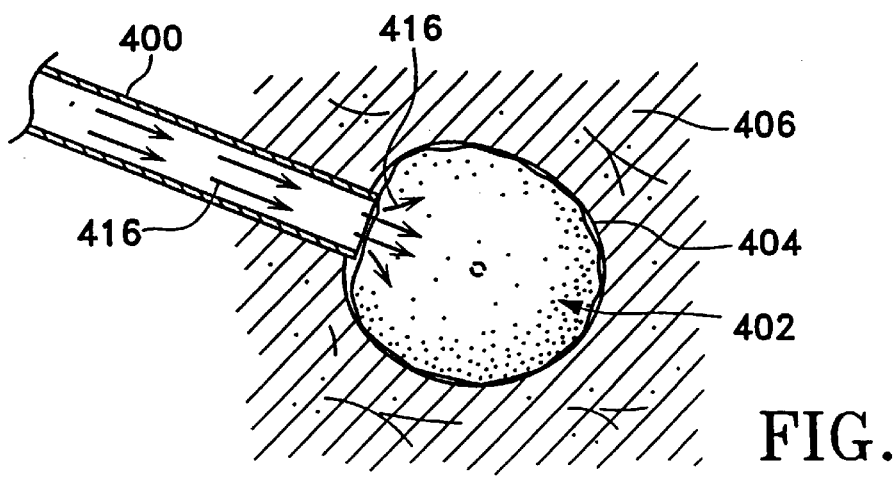

FIGS. 4G–4I show another method of delivering the marking device (402) into the tissue cavity (404) by using the bio-compatible fluid (416) as the force to deliver the marking device (402) into the tissue cavity (404).

FIG. 4G details the marking device (402) prior to delivery into the tissue cavity (404). FIG. 4H illustrates flow of the bio-compatible fluid (416) in the access device (400), the fluid (416) flow then pushes the marking device (402) out of the access device (400).

FIG. 4I shows the delivery device (400) continuing to deliver the bio-compatible fluid (416) into the cavity (404). The fluid (416) aids the marking device (402) in expanding to substantially fill the cavity (404). In this example, the bio-compatible fluid (416) is delivered after the placement of the marking device (402) in the cavity (404) although the invention is not limited to the continued delivery of the fluid (416).

Figure 4J:
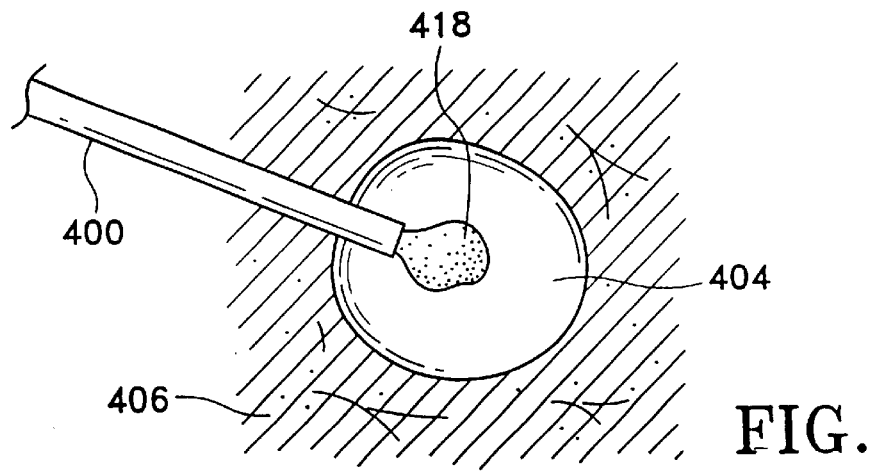
FIGS. 4J–4L illustrate a method of marking a biopsy tissue cavity with the device of the present invention wherein the body material of the marking device is deposited into the biopsy cavity prior to the placement of the marker within the biopsy device.
Figure 4K:
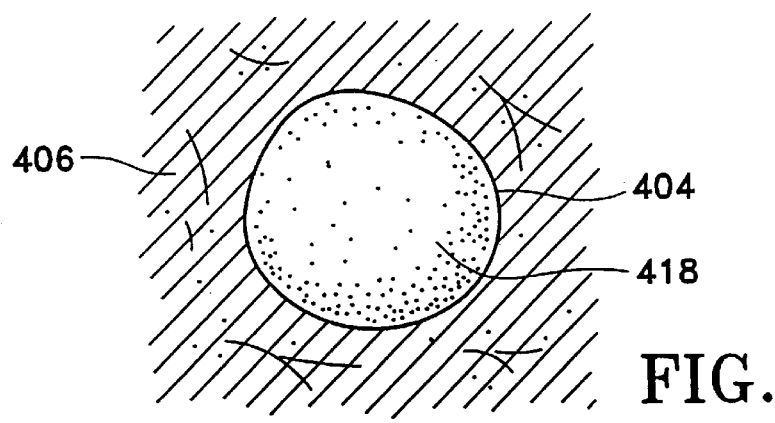

FIG. 4J–4K shows the method of delivering the body (418) of the cavity marking device directly into the cavity (404) prior to the placement of the marker (410) in the device (402).

Figure 4L:
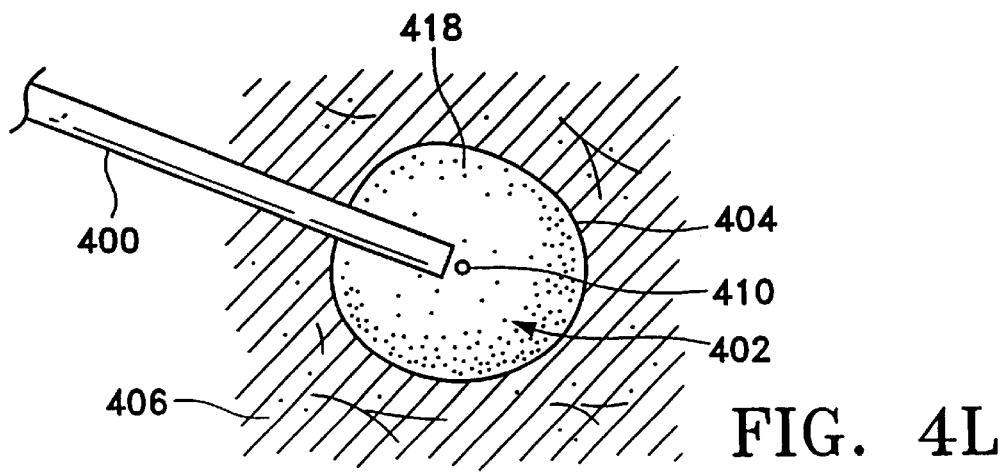

FIG. 4J shows the deposit of the body material (418) into the cavity (404). In this case the body material (418) may be a gel type material as described above. FIG. 4K details the filling of the cavity (404) with the body material (418). At this point, the delivery device (not shown in FIG. 4K) may be withdrawn. FIG. 4L details the placement of the marker (410) into the body material (418).

FIGS. 5A–5E show yet another version of the invention in which a marker, preferably consisting of a radiopaque or echogenic wire, is deployed alone into a tissue cavity without the use of any body. In this device, the marker can be made of a shape memory material, such as a nickel-titanium alloy, which when deployed into the biopsy cavity, assumes a predetermined configuration to substantially fill the cavity, mark the cavity location and margin, and indicate the orientation of the marker inside the cavity.

Figure 5A:
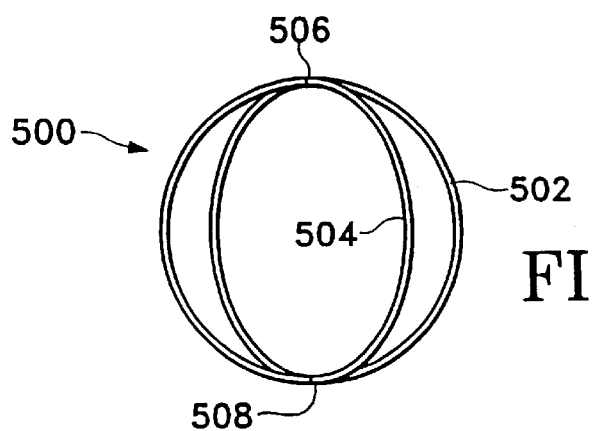
FIGS. 5A–B illustrate a spherical wire marking device for deployment without a filler body into a tissue cavity.
Figure 5B:
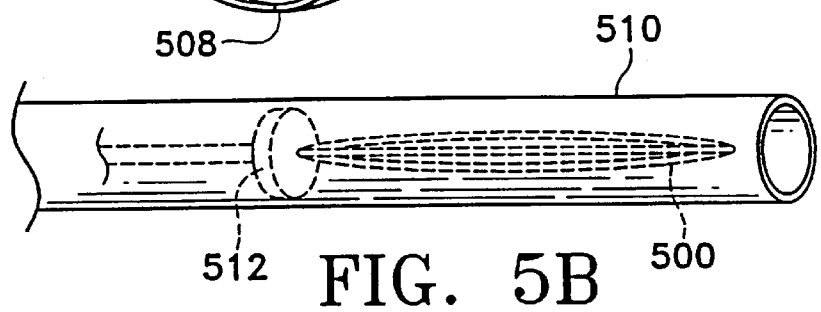

In FIG. 5A, marker (500) is a three-dimensional sphere consisting of two rings (502), (504) pivotally connected at ends (506), (508) so to assume a spherical shape. Such a marker can be made of a shape memory metal so that when it is placed in a deployment tube (510) shown in FIG. 5B, marker (500) assumes a collapsed profile suitable for deployment through tube (510) by pusher (512). Upon exiting into the tissue cavity (not shown), marker (500) assumes the spherical shape of FIG. 5A to fill the cavity. The marker (500) may also be shaped into any similar shape such as an ellipsoidal shape.

Figure 5C:
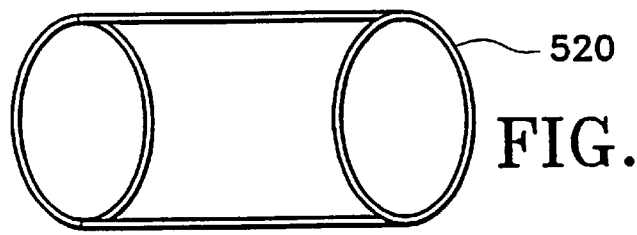
FIG. 5C illustrates a cylindrical wire marking device for deployment without a filler body into a tissue cavity.

Turning now to FIG. 5C, a marker (520) in the form of a wire cylinder is shown. Again, this device is structurally configured to assume the depicted cylindrical configuration when deployed in the tissue cavity, but may be (as described above) "collapsed" into a deployment tube for percutaneous delivery. This device is especially suitable for marking the distal and proximal ends of the tissue cavity due to its asymmetrical shape.

Figure 5D:
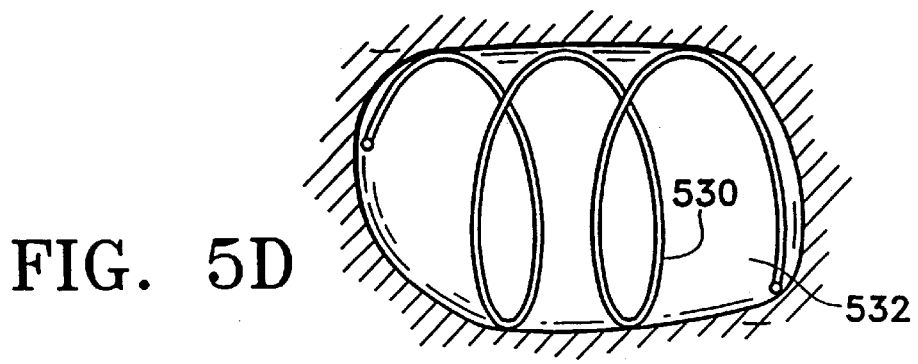
FIGS. 5D–E illustrate a helical coil wire marking device for deployment without a filler body into a tissue cavity.
Figure 5E:
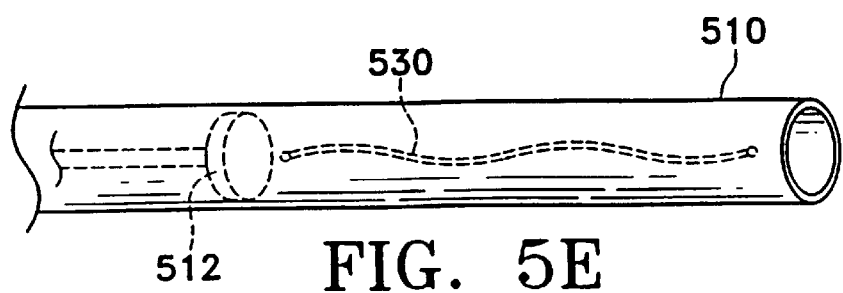

FIG. 5D shows a shape memory marker (530) in the form of a helical coil deployed into tissue cavity (532). Again, as seen in FIG. 5E, such a marker (530) may be deployed through delivery tube (510) by pusher (512) in a substantially elongated, straightened form, only to substantially assume the shape of the cavity (532) as shown in FIG. 5D. Any suitable delivery device or pusher (512) capable of deploying marker (530) into cavity (532) is within the scope of this invention.

Each of the markers shown in FIGS. 5A–5E is preferably a shape memory material coated or supplemented with a radiopacity-enhancing material, such as gold, platinum, or any other radiopaque material herein discussed. The markers may singly, or in combination with being radiopaque, be echogenic or be made echogenic by any of the materials or methods herein described.

From the foregoing, it is understood that the invention provides an improved subcutaneous cavity marking device and method. While the above descriptions have described the invention for use in the marking of biopsy cavities, the invention is not limited to such. One such application is evident as the invention may further be used as a lumpectomy site marker. In this use, the cavity marking device yield an improved benefit by marking the perimeter of the lumpectomy cavity.

The invention herein has been described by examples and a particularly desired way of practicing the invention has been described. However, the invention as claimed herein is not limited to that specific description in any manner. Equivalence to the description as hereinafter claimed is considered to be within the scope of protection of this patent.

We claim as our invention:

1. A subcutaneous cavity marking device comprising:
   (a) at least one filler body comprising a resilient bioabsorbable material, and
   (b) at least one detectable marker attached to said filler body and adapted to mark a center of said filler body, wherein said marker is mammographic.

2. The device of claim 1 wherein the at least one marker comprises a non-bioabsorbable material.

3. The device of claim 2 wherein the marker comprises a material selected from the group consisting of platinum, iridium, nickel, tungsten, tantalum, gold, silver, rhodium, titanium, alloys thereof, and stainless steel.

4. The device of claim 1 wherein the at least one marker comprises a second bioabsorbable material.

5. The device of claim 4 wherein the second bioabsorbable material comprises a polymer having a radiopaque additive.

6. The device of claim 5 wherein the radiopaque additive is selected from the group consisting of barium-containing compounds, bismuth-containing compounds, powdered tantalum, powdered tungsten, barium carbonate, bismuth oxide, and barium sulfate.

7. The device of claim 1 wherein the at least one marker is radiopaque.

8. The device of claim 1 wherein the at least one body is radiopaque.

9. The device of claim 1 wherein the at least one marker is echogenic.

10. The device of claim 1 wherein the at least one body is echogenic.

11. The device of claim 1 wherein the at least one body is mammographic.

12. The device of claim 1 wherein the at least one body is palpable.

13. The device of claim 12 wherein after insertion of said device into a patient said marker is not locatable by tactile detection.

14. The device of claim 1 wherein the marker is located within an interior of the at least one body.

15. The device of claim 1 wherein the marker is substantially located within a geometric center of the at least one body.

16. The device of claim 1 additionally comprising a pain killing substance.

17. The device of claim 1 additionally comprising a hemostatic substance.

18. The device of claim 1 wherein the bioabsorbable material is selected from the group consisting of collagen, regenerated cellulose, synthetic polymers and synthetic proteins.

19. The device of claim 1 wherein the marker has a form of a sphere.

20. The device of claim 19 wherein the sphere is hollow.

21. The device of claim 1 wherein the marker has a form of a band.

22. The device of claim 1 wherein the marker comprises a suture.

23. The device of claim 1 wherein the marker comprises a wire.

24. The device of claim 1 wherein the marker has a distinguishing mark.

25. The device of claim 1 wherein the marker is fixedly attached to the at least one body.

26. The device of claim 25 wherein the marker is woven to the at least one body.

27. The device of claim 1 wherein the marker is radioactive.

28. The device of claim 1 wherein the at least one body is radioactive.

29. The device of claim 1 wherein the at least one body is substantially spherical.

30. The device of claim 1 wherein the at least one body is substantially cylindrical.

31. The device of claim 1 wherein the at least one body is has a substantially irregular shape.

32. The device of claim 1 wherein the at least one body comprises a plurality of pores.

33. The device of claim 32 wherein the pores are configured to promote tissue growth in a preferred orientation.

34. The device of claim 1 wherein the at least one filler body additionally comprises a bio-compatible liquid.

35. The device of claim 1 wherein said filler body further comprises a palpable shell.

36. The device of claim 35 wherein said shell is bioabsorbable and degrades when implanted within a patient's body, after said shell degrades said shell is no longer palpable.

37. The device of claim 36 wherein said shell is configured to degrade over a period of time.

38. The device of claim 37 wherein said period of time is less than 1 year.

39. The device of claim 37 wherein said period of time is between 2 and 6 months.

40. The device of claim 37 wherein said period of time is about 3 months.

41. The device of claim 1 wherein after a period of time said body is not palpable.

42. The device of claim 41 wherein said period of time is approximately 3 months.

43. A subcutaneous cavity marking device comprising:
   (a) at least one filler body comprising a resilient bioabsorbable material, wherein the at least one body is mammographic, and
   (b) at least one detectable marker attached to said filler body and adapted to mark a center of said filler body.

44. The device of claim 43 wherein the at least one marker comprises a non-bioabsorbable material.

45. The device of claim 44 wherein the marker comprises a material selected from the group consisting of platinum, iridium, nickel, tungsten, tantalum, gold, silver, rhodium, titanium, alloys thereof, and stainless steel.

46. The device of claim 43 wherein the at least one marker comprises a second bioabsorbable material.

47. The device of claim 46 wherein the second bioabsorbable material comprises a polymer having a radiopaque additive.

48. The device of claim 47 wherein the radiopaque additive is selected from the group consisting of barium-containing compounds, bismuth-containing compounds, powdered tantalum, powdered tungsten, barium carbonate, bismuth oxide, and barium sulfate.

49. The device of claim 43 wherein the at least one marker is radiopaque.

50. The device of claim 43 wherein the at least one body is radiopaque.

51. The device of claim 43 wherein the at least one marker is echogenic.

52. The device of claim 43 wherein the at least one body is echogenic.

53. The device of claim 43 wherein the at least one body is palpable.

54. The device of claim 53 wherein after insertion of said device into apatient said marker is not locatable by tactile detection.

55. The device of claim 43 wherein the marker is located within an interior of the at least one body.

56. The device of claim 43 wherein the marker is substantially located within a geometric center of the at least one body.

57. The device of claim 43 additionally comprising a pain killing substance.

58. The device of claim 43 additionally comprising a hemostatic substance.

59. The device of claim 43 wherein the bioabsorbable material is selected from the group consisting of collagen, regenerated cellulose, synthetic polymers and synthetic proteins.

60. The device of claim 43 wherein the marker has a form of a sphere.

61. The device of claim 60 wherein the sphere is hollow.

62. The device of claim 43 wherein the marker has a form of a band.

63. The device of claim 43 wherein the marker comprises a suture.

64. The device of claim 43 wherein the marker comprises a wire.

65. The device of claim 43 wherein the marker has a distinguishing mark.

66. The device of claim 43 wherein the marker is fixedly attached to the at least one body.

67. The device of claim 66 wherein the marker is woven to the at least one body.

68. The device of claim 43 wherein the marker is radioactive.

69. The device of claim 43 wherein the at least one body is radioactive.

70. The device of claim 43 wherein the at least one body is substantially spherical.

71. The device of claim 43 wherein the at least one body is substantially cylindrical.

72. The device of claim 43 wherein the at least one body is has a substantially irregular shape.

73. The device of claim 43 wherein the at least one body comprises a plurality of pores.

74. The device of claim 73 wherein the pores are configured to promote tissue growth in a preferred orientation.

75. The device of claim 43 wherein the at least one filler body additionally comprises a bio-compatible liquid.

76. The device of claim 43 wherein said filler body further comprises a palpable shell.

77. The device of claim 76 wherein said shell is bioabsorbable and degrades when implanted within a patient's body, after said shell degrades said shell is no longer palpable.

78. The device of claim 77 wherein said shell is configured to degrade over a period of time.

79. The device of claim 78 wherein said period of time is less than 1 year.

80. The device of claim 78 wherein said period of time is between 2 and 6 months.

81. The device of claim 78 wherein said period of time is about 3 months.

82. The device of claim 43 wherein after a period of time said body is not palpable.

83. The device of claim 82 wherein said period of time is approximately 3 months.

84. A method of marking a tissue cavity having a margin in a mammalian body, comprising:
  (a) subcutaneously accessing the cavity via a delivery device,
  (b) introducing a biocompatible liquid in a remotely-detectable marker having a predetermined shape; and thereafter
  (c) deploying the marker through the delivery device into the cavity,
    wherein upon delivery into the cavity the marker assumes a predetermined three-dimensional configuration so to (1) substantially fill the cavity, (2) mark the cavity margin, and (3) indicate the orientation of the marker inside the cavity.

85. The method of claim 84 wherein the marker is bioabsorbable.

86. The method of claim 84 wherein the marker is radiopaque.

87. The method of claim 84 wherein the marker is echogenic.

88. The method of claim 84 wherein the marker comprises a wire.

89. The method of claim 85 wherein the wire comprises a shape memory material.

90. The method of claim 84 wherein the marker comprises a material selected from the group consisting of platinum, iridium, nickel, tungsten, tantalum, gold, silver, rhodium, titanium, alloys thereof, and stainless steel.

91. The method of claim 84 wherein the marker is capable of emitting radioactive energy.

92. The method of claim 84 wherein the marker is a helical coil.

93. The method of claim 84 wherein the marker defines a volume having a substantially spherical shape when the marker is deployed inside the cavity.

94. The method of claim 84 wherein the marker defines a volume comprising a substantially cylindrical shape when the marker is deployed inside the cavity.

95. The method of claim 84 wherein the marker defines a volume comprising a random shape when the marker is deployed inside the cavity.

96. The method of claim 84 wherein the delivery device uses a hydraulic force to deploy the marker.

97. The method of claim 84 wherein the delivery device comprises a biopsy device.

98. A method of marking a tissue cavity having a margin in a mammalian body, comprising:
 (a) subcutaneously accessing the cavity via a delivery device,
 (b) deploying a remotely detectable marker having a predetermined shape through the delivery device into the cavity, and thereafter
 (c) introducing a biocompatible liquid in the marker, wherein upon delivery into the cavity the marker assumes a predetermined three-dimensional configuration so to (1) substantially fill the cavity, (2) mark the cavity margin, and (3) indicate the orientation of the marker inside the cavity.

99. The method of claim 98 wherein the bio-compatible liquid is introduced to the marker via the delivery device.

100. The method of claim 98 wherein the marker is bioabsorbable.

101. The method of claim 98 wherein the marker is radiopaque.

102. The method of claim 98 wherein the marker is echogenic.

103. The method of claim 98 wherein the marker comprises a wire.

104. The method of claim 103 wherein the wire comprises a shape memory material.

105. The method of claim 104 wherein the marker comprises a material selected from the group consisting of platinum, iridium, nickel, tungsten, tantalum, gold, silver, rhodium, titanium, alloys thereof, and stainless steel.

106. The method of claim 104 wherein the marker is capable of emitting radioactive energy.

107. The method of claim 104 wherein the marker is a helical coil.

108. The method of claim 104 wherein the marker defines a volume having a substantially spherical shape when the marker is deployed inside the cavity.

109. The method of claim 104 wherein the marker defines a volume comprising a substantially cylindrical shape when the marker is deployed inside the cavity.

110. The method of claim 104 wherein the marker defines a volume comprising a random shape when the marker is deployed inside the cavity.

111. The method of claim 104 wherein the delivery device comprises a biopsy device.

* * * * *